United States Patent [19]

Winslow, Jr.

[11] 4,056,968
[45] Nov. 8, 1977

[54] HYDROGEN PROBE SYSTEM

[75] Inventor: Joseph D. Winslow, Jr., Houston, Tex.

[73] Assignee: Petrolite Corporation, St. Louis, Mo.

[21] Appl. No.: 643,284

[22] Filed: Dec. 22, 1975

[51] Int. Cl.$^2$ ............................................. G01N 7/10
[52] U.S. Cl. .................................... 73/19; 23/253 C
[58] Field of Search ................. 73/19, 23, 392, 411, 73/416, 418; 23/230 C, 232 R, 232 E, 253 C, 254 R, 254 E; 55/158

[56] References Cited

U.S. PATENT DOCUMENTS

| 2,231,570 | 2/1941 | Ryder | 73/411 |
|---|---|---|---|
| 2,671,336 | 3/1954 | Hulsberg | 73/23 |
| 3,949,593 | 4/1976 | Oertle | 73/19 |

FOREIGN PATENT DOCUMENTS

| 1,165,432 | 10/1969 | United Kingdom | 73/19 |

OTHER PUBLICATIONS

Marsocci, *Semiconductor Products*, "A Survey of Semiconductor Devices and Circuits in Computers," Jan. 1961, pp. 31–37.

*Primary Examiner*—Jerry W. Myracle
*Assistant Examiner*—Stephen A. Kreitman
*Attorney, Agent, or Firm*—Sidney B. Ring; Hyman F. Glass

[57] ABSTRACT

A hydrogen probe system measuring hydrogen gas produced in the corrosion of steel, both in volume and rate, with a relatively simple construction, rapid installation at any location and trouble-free operation for extended periods of time without supervision. The probe system has a ferrous metal body enclosing a cavity wherein hydrogen gas is collected under superatmospheric pressure. The accumulated hydrogen gas is periodically vented by a valve operated between two pressure set-points with a "snap action" function by a control mechanism. Each actuation of the valve is a readout function of hydrogen gas accumulating in the cavity representing total gas volume or the rate of gas generation.

10 Claims, 3 Drawing Figures

HYDROGEN PROBE SYSTEM

BACKGROUND OF THE INVENTION

1. Field of the Invention

This invention relates to measuring and testing of corrosion processes, and it relates more particularly to a probe system for measuring molecular hydrogen gas created by the corrosion of ferrous metals.

2. Description of the Prior Art

It is often desirable to determine the rates at which ferrous metals corrode within a corrodant, such as a corrosive aqueous liquid. For example, corrosion inhibitors are added to aqueous liquids to reduce the corrosion of exposed metals. Instruments are used to measure the rates at which these metals corrode so that the effectiveness of inhibitor addition can be determined. One measurement of the rate of corrosion upon ferrous metals involves the determination of the amount of molecular hydrogen created by the corrosion reaction of a ferrous metal exposed to a corrodant. For example, a steel sidewall of a pipeline carrying a corrodant, such as hydrogen sulfide in water, has a corrosion reaction creating atomic hydrogen which diffuses through the sidewall and released exteriorly as molecular hydrogen gas. Escape of the molecular hydrogen gas from the sidewall permits the corrosion reaction to continue. However, the molecular hydrogen gas escaping the sidewall can oftentimes build up to a sufficient pressure causing physical injury such as blistering and rupturing of the sidewall's exterior surface.

Various measurements systems have been proposed for the measurement of the molecular hydrogen gas produced by the corrosion reaction. For this purpose, a probe may be inserted through the sidewall of the pipeline and arranged to measure the molecular hydrogen gas pressure buildup within the probe. For this purpose, the probe has a ferrous metal body in which there is formed a cavity. The corrosion reaction produced by the corrodant surrounding the probe causes molecular hydrogen gas to accumulate within the cavity. A pressure gauge mounted atop the probe indicates the actual pressure of the hydrogen gas accumulating within the cavity. For example, in very active corrodants, the pressure buildup of such a probe can reflect hydrogen gas accumulations within the cavity from an initial 15 psi to about 100 psi within a 24-hour period. The probe carries a manual venting valve so that the pressure can be released from the cavity when the pressure limits of the gauge are reached. Thus, this type of hydrogen measurement probe must be employed in a supervised manner wherein the operator can periodically record the readings of the probe and also vent hydrogen gas as necessary to prevent the destruction of the pressure gauge. This type of hydrogen measurement probe is simple and relatively inexpensive but has not found extensive utilization in the industry because of the requirement for relatively constant supervision.

Another type of hydrogen measurement probe avoids the supervision problem but employs a sophisticated gas ionization instrumentation principle. In this probe, the hydrogen gas is vented in a relatively continuous manner from the cavity within the probe body. The vented gas flows through an ionization chamber and detector sensor whose output is measured upon a scalar instrument indicating both total gas volume and rate of gas flow. This probe and readout instrumentation is relatively accurate, very expensive and dependable, but requires careful calibration and complicated installation. Also, this probe is relatively delicate for use unattended within oil fields, refineries and chemical plants.

The hydrogen probe system of the present invention is arranged to provide the simplicity of construction and operation of first mentioned probe with the utility and accuracy of the second mentioned hydrogen measurement probe but without its great expense and other accompanying problems.

SUMMARY OF THE INVENTION

In accordance with this invention, there is provided a hydrogen probe system having a ferrous metal body with an enclosed fluid-tight internal cavity for collecting hydrogen gas under superatmospheric pressure produced by action of a corrodant on the body. A pressure sensor reflects the accumulation of superatmospheric pressurized hydrogen gas within the cavity. A control means responsive to the pressure sensor is associated with a valve to vent hydrogen gas from the cavity. The control means produces a "snap action" opening and closing of the valve for reducing periodically the hydrogen pressure in the cavity from a certain superatmospheric pressure (50 psi) to a certain lesser superatmospheric pressure (15 psi). A readout device indicates the actuation of the valve as a function of the hydrogen gas accumulating in the cavity. In a preferred embodiment, the readout device includes a totalizer for indicating the total actuations (hydrogen gas volume) of the valve and a differentiator for indicating the number of actuations of the valve per unit time (hydrogen gas rate).

DESCRIPTION OF SPECIFIC EMBODIMENTS

Figure 1:
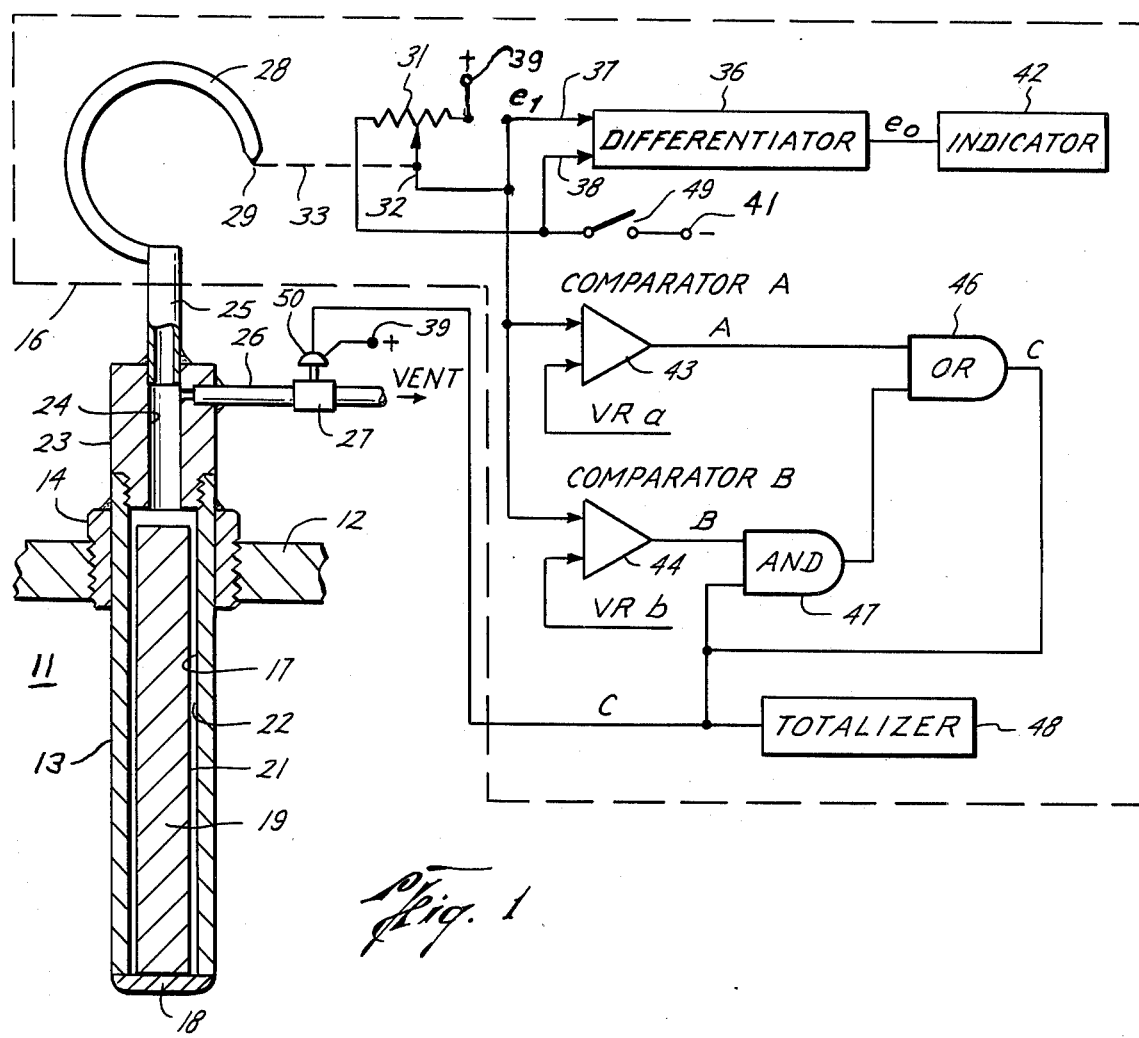
FIG. 1 is a vertical section and an electrical schematic in illustration of one embodiment of the hydrogen probe system of the present invention.

FIG. 1 illustrates one embodiment of the hydrogen probe system 11 of the present invention. The system 11 is threadedly secured into a pipe wall 12 with the body 13 exposed to a corrodant, such as an aqueous stream containing hydrogen sulfide. The pipe wall 12 can be the steel sidewall of an exposed pipeline. The body 13 has an integral adapter 14 carried at its upper extremity for threadedly engaging the pipe wall 12. Other arrangements for adapting the body 13 to the exposure of a corrodant may be employed, if desired. The probe system 11 is comprised basically of the body 13 and an instrumentation package 16 carried at one end of the body 13. The instrumentation package 16 is shown within the chainline enclosure and will be described in more detail relative to FIG. 2.

The body 13 is formed of a ferrous metal such as steel and can be machined from an elongated piece of suitable bar stock. The body 13 is provided with a central opening 17 which is sealed at its lower extremity by end cap 18. The end cap 18 integrally carries an upstanding metal filler piece 19 whose side surfaces 21 are spaced a small distance from the opening 17. As a result, the intervening space between these elements of the body 13 and filler piece 19 form a cavity 22 of relatively small volummetric dimension. The volummetric capacity of the cavity 22 is adjusted to conform to the other elements of the present probe system as will be apparent from the forthcoming discussion. In addition, the cavity 22 can contain a solid, porous matrix material such as clay or aluminum to further decrease its volummetric capacity.

The upper portion of the body 13 is closed in a suitable manner that the cavity 22 is enclosed in a fluid-tight relationship relative to the atmosphere. For example, the open end of the body 13 carries internal threads in which are received a nipple 23. The nipple 23 has an internal passageway 24 in fluid communication with the cavity 22. An outlet pipe 26 extends into the channel 24 and carries a valve 27 which is arranged to vent from the body 13 the hydrogen gas accumulating within the cavity 22. Preferably, the pipe 26 is of a capillary type so that relatively small volumes (e.g. 0.3 cc/min.) of hydrogen gas may be vented under controlled flow conditions. The upper extremity of the nipple 23 carries a pressure sensor 25 which is employed for reflecting the magnitude of superatmospheric pressure of hydrogen gas in the cavity 22.

The pressure sensor 25 is designed to provide an output function which corresponds to the magnitude of superatmospheric pressure of the hydrogen gas in the cavity 22. The pressure sensor 25 is contained within the instrumentation package 16.

Preferably, the pressure sensor 25 is a Bourdon tube 28 connected into the fluid channel 24 within the nipple 23. The Bourdon tube 28 is selected relative to the cavity 22 so that the free end 29 moves spacially through a suitable distance as the output function in response to hydrogen gas accumulating as superatmospheric pressure in the cavity 22. For example, the movement by the free end 29 of 5 millimeters between hydrogen gas pressure levels of 25 and 50 psi is suitable for the present hydrogen probe system. The output function of the Bourdon tube 28 (or other pressure sensor) is applied to a control means which also resides within the instrumentation package 16. This control means provides, by mechanical, electrical or other actuating mechanism, the "snap action" opening and closing of the valve 27 for venting the hydrogen gas in the cavity 22 from a certain superatmospheric pressure to a certain lesser superatmospheric pressure. In a preferred form, the output function is employed as an electrical signal. The electrical signal is applied in the control means to a state-of-the-art solid state circuitry forming the control element, and an electromechanical valve actuator, 50 which is operably connected to the electromagnetic operated valve 27. The solid state circuitry places the control element into and out of conduction for energizing the electromechanical valve actuator responsively to first and second levels of the electrical signal representing the hydrogen gas in the cavity 22 being vented from the certain superatomospheric pressure to the certain lesser superatmospheric pressure.

More particularly, the free end 29 of the Bourdon tube 28 is applied to a resistive transducer to provide an electrical signal $e_1$. The resistive transducer can be a small slidewire pot 31 having a moveable arm 32 connected by mechanical link 33 to the free end 29 of the Bourdon tube 28. The pot 31, connected to power terminals 39 and 41, is selected so that the desired superatmospheric pressure levels of the hydrogen gas before and after venting from the cavity 22 are adjacent the limits of travel of the arm 32. The electrical signal $e_1$ from the pot 31 is applied to a differentiator 36 which has conventional inputs 37 and 38, with the input 37 receiving the electrical signal $e_1$ and the input 38 connected to the negative power terminal 49.

The differentiator 36 can be of any form which performs the differential function on electrical signal $e_1$ to produce an electrical output signal $e_o = dp/dt$. The electrical output signal $e_o$ is applied to an indicator 42 which may be a digital voltmeter for indicating the number of "ventings" of the valve 27 per unit time.

The electrical signal $e_1$ is also employed to control operation of the valve 27 and accumulate the total number of "valvings" or counts for any selected time period. Particularly, the electrical signal $e_1$ is applied to comparators 43 and 44 which are referenced to low and high pressure set points represented by reference voltages $VR_a$ and $VR_b$, (e.g., 15 and 50 psi). The outputs A and B of the comparators are applied to gates 46 and 47 which combine in the conventional "AND", and "OR" functions to produce output C. The output C appears, in the preferred embodiment, periodically coincident with the pressure in the cavity 22 being vented between the certain superatmospheric pressure and the certain lesser superatmospheric pressure (e.g., 50 psi–15 psi). The output C is applied to a totalizer 48 which can be a counter reflecting the total "ventings" of valve 27 for a selected time base by the function, counts = A + B·C. Also, the periodic output C is used to activate electrically the valve 27. Preferably, the valve 27 is vented in the absence of output C. This is an important feature of the present probe system since with power disconnected from the terminals 39 and 41, the valve 27 is open and hydrogen gas is continuously vented from the probe system 11 so that it cannot accumulate into sufficiently destructive pressures to damage the pressure sensor or Bourdon tube 28.

If desired, the application of power to the terminals 39 and 41 is controlled by an on-off switch 49 in series with the negative power lead 41. Thus, opening the switch 49 disconnects power from the control means and opens the valve 27 for continuously venting pressurized hydrogen from the cavity 22. Closing the switch 49 places the control means into operation when it is desired to make measurements of hydrogen gas accumulation in the cavity 22.

The valve 27 preferably has an electromagnetic activator 50 so that it is closed only upon energization through output C in the preferred embodiment of the present hydrogen probe system. However, the activator 50 may be arranged in the reverse operation so that the valve 27 is opened only upon energization. In either event, the hydrogen probe system operates in an identical manner except that in the latter instance, placing the switch 49 in the "off" position allows hydrogen gas to accumulate within the cavity 22.

Figure 2:
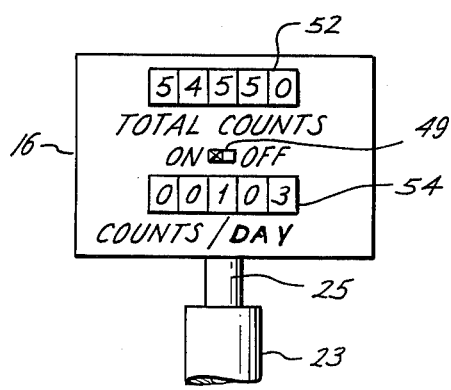
FIG. 2 is a partial elevation illustrating the readout devices and operating switch of the probe system of FIG. 1.

Referring briefly to FIG. 2, a readout 52 of totalizer 48 is displayed at the upper portion of the instrumentation package 16. The readout 54 of the indicator 42 is displayed at the lower portion of package 16. The off-on switch 49 is positioned intermediate the readouts. Selection of the components within the instrumentation package 16 permits a high degree of miniaturization. The physical size of the instrumentation package 16 can easily be of a size comparable to the usual pressure gauge or, for example, within the dimensions of 50×75×200 mm. Since the power source usually is a small battery, the entire probe system 11 is self-contained, may be placed easily in any positiion or location and operated without attendant supervision. At the beginning of a desired monitoring period, the readouts 52 and 54 are noted. Then, the switch 49 is placed in the "on" position. The hydrogen probe system 11 is left to operate for the desired length of time or until the operator returns to note the readouts 52 and 54. The only time limit will be the useful life of the battery forming the power source.

Figure 3:
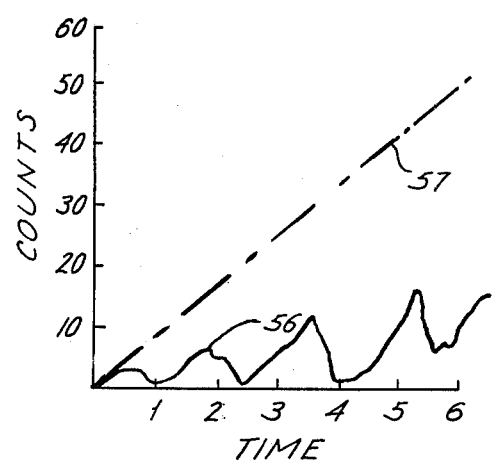
FIG. 3 is a graphical representation of the readout information obtained from the probe system of FIG. 1.

Referring to FIG. 3, there is indicated graphically a representation of the correlation between the readouts 52 and 54. On the ordinate are indicated total counts and on the abscissa is indicated time in a convenient scale. The various count rates of readout 54 are indicated in a curve 56 and vary numerically with time depending on actual accumulation volume of hydrogen gas in the cavity 22. The readout 52 produces a total count rate corresponding to the volummetric accumlation of hydrogen within the cavity 22 within a selected time. This is represented by the straight line 57 on the graph which is also indicative of corrosion rate magnitudes. Thus, both the total volume and the volummetric rate of the hydrogen gas accumulating within the cavity 22 (and vented by the valve 27) can be readily determined by the present hydrogen probe system 11.

An important feature of the present hydrogen probe system resides in the operation of the valve 27 with a "snap action" function. The valve 27 obviously must contain hydrogen gas under superatmospheric pressure and yet be opened and closed in a reliable fashion. This requires a positive opening and a positive closing of the valve mechanism. For this purpose, a "snap action" actuation is essentially a requirement for satisfactory operation.

Various modifications and alterations in the described hydrogen probe system will be apparent to those skilled in the art from the foregoing description which do not depart from the spirit of the invention. For this reason, these changes are desired to be included within the scope of the appended claims. The appended claims define the present invention; the foregoing description is to be employed for setting forth the present embodiments as illustrative and not limited in nature.

What is claimed is:

1. A hydrogen probe system comprising:
   a. a ferrous metal probe body adapted to be exposed to a corrodant, said body having an enclosed fluid-tight internal cavity for collecting hydrogen gas under superatmospheric pressure buildup due to the accumulated hydrogen gas produced by action of the corrodant on said body;
   b. a pressure sensor carried on said body and connected by a fluid channel to said cavity, said sensor providing an output function which corresponds to the superatmospheric pressure of the hydrogen gas accumulated in said cavity;
   c. valve means carried on said body for venting hydrogen gas from said cavity;
   d. control means receiving the output function and with a snap action opening and closing said valve means for venting to the atmosphere the hydrogen gas in said cavity from a certain superatmospheric pressure buildup to a certain lesser superatmospheric pressure; and
   e. readout means indicating actuation of said valve means as a function of hydrogen gas accumulating in said cavity.

2. The hydrogen probe system of claim 1 wherein said readout means includes a totalizer means operated by a signal from said control means for indicating the total actuations of said valve means and a differentiator means operated by the output function of said pressure sensor for indicating the number of actuations of said valve means per unit time.

3. The hydrogen probe system of claim 1 wherein the output function is an electrical signal, and said control means having solid state circuitry with "And" and "Or" gates associated in said control means, and an electromechanical valve actuator operably connected to said valve means whereby said solid state circuitry within said control means energizes and de-energizes said electromechanical valve actuator responsive to first and second levels of the electrical signal representing the hydrogen gas in said cavity being at the certain superatmospheric pressure and the certain lesser superatmospheric pressure.

4. A hydrogen probe system comprising:
   a. a ferrous metal probe body adapted to be exposed to a corrodant, said body having an enclosed fluid-tight internal cavity for collecting hydrogen gas under superatmospheric pressure produced by action of the corrodant on said body;
   b. a pressure sensor carried on said body and connected by a fluid channel to said cavity, said sensor providing an output function which corresponds to the superatmospheric pressure of the hydrogen gas in said cavity, wherein said pressure sensor is a Bourdon tube integrally carried on said body, said Bourdon tube having a free end which moves spacially in response to hydrogen gas accumulating in said cavity, and the movement of said free end is the output function;
   c. valve means carried on said body for venting hydrogen gas from said cavity;
   d. control means receiving the output function and with a snap action opening and closing said valve means for venting to the atmosphere the hydrogen gas in said cavity from a certain superatmospheric pressure to a certain lesser superatmospheric pressure; and
   e. readout means indicating actuation of said valve means as a function of hydrogen gas accumulating in said cavity.

5. The hydrogen probe system of claim 4 wherein the movement of said free end is applied to a resistive transducer for conversion of the output function into an electrical signal applied to said control means for operating said valve means with snap action opening and closing actuation.

6. A hydrogen probe system comprising:
   a. a ferrous metal probe body adapted to be exposed to a corrodant, said body having an enclosed fluid-tight internal cavity for collecting hydrogen gas under superatmospheric pressure produced by action of the corrodant on said body;
   b. a Bourdon tube carried integrally on said body and connected by a fluid channel to said cavity, said Bourdon tube having a free end which moves spacially in an output function in response to hydrogen gas accumulating in said cavity;
   c. electrically operated valve means carried on said body for venting hydrogen gas to the atmosphere from said cavity;
   d. resistive transducer means converting the output function into an electrical signal;
   e. control means receiving the electrical signal and having an electrical circuit for actuating with a snap action said valve means in opening thereof responsive to first and second levels of the electrical signal representing the hydrogen gas in said cavity being vented from a certain superatmospheric pressure to a certain lesser atmospheric pressure; and f. readout means indicating actuation of said valve means as a function of hydrogen gas accumulating in said cavity.

7. The hydrogen probe system of claim 6 wherein said readout means includes a totalizer means for indicating the total actuations of said valve means and a differentiator means for indicating the number of actuations of said valve means per unit time.

8. The hydrogen probe system of claim 6 wherein said control means has a solid state circuitry within said control means electrically connected to said valve means whereby said solid state circuitry selectively energizes and de-energizes said valve means with a snap action responsive to first and second levels of the electrical signal representing the hydrogen gas in said cavity being at the certain superatmospheric pressure and the certain lesser superatmospheric pressure.

9. The hydrogen probe system of claim 6 wherein said control means has a solid state circuitry within said control means to receive the electrical signal from said resistive transducer means and an output circuit including first and second comparators and gate means, an electromechanical valve actuation means and voltage source, said output circuit connected to said valve means whereby said first and second levels of the electrical signal provide AND/OR outputs from said gate means to open and close said valve means with a snap action as the hydrogen gas in said cavity is, respectively, at the certain superatmospheric pressure and the certain lesser superatmospheric pressure.

10. The hydrogen probe system of claim 6 wherein said readout means receives the first and second levels of the electrical signal and applies same to a totalizer means for indicating the total actuation of said valve means and to a differentiator means for indicating the number of actuations of said valve means per unit time.

* * * * *